United States Patent [19]

Engelhardt et al.

[11] Patent Number: 5,182,312

[45] Date of Patent: Jan. 26, 1993

[54] HYDROPHILIC, SWELLABLE POLYMERS

[75] Inventors: Friedrich Engelhardt, Frankfurt am Main; Gerlinde Ebert, Dreieich/Offenthal, both of Fed. Rep. of Germany

[73] Assignee: Cassella Aktiengesellschaft, Frankfurt am Main, Fed. Rep. of Germany

[21] Appl. No.: 589,808

[22] Filed: Sep. 24, 1990

[30] Foreign Application Priority Data

Oct. 6, 1989 [DE] Fed. Rep. of Germany ....... 3933351

[51] Int. Cl.$^5$ .......................... C08J 9/00; C08F 38/00
[52] U.S. Cl. ..................................... 521/149; 521/150
[58] Field of Search ................. 521/149, 150

[56] References Cited

U.S. PATENT DOCUMENTS

| | | | |
|---|---|---|---|
| 3,886,125 | 5/1975 | Chromecek | 521/149 |
| 4,190,713 | 2/1980 | Kraemer et al. | 521/149 |
| 4,224,415 | 9/1980 | Meitzner et al. | 521/149 |
| 4,535,098 | 8/1985 | Evani et al. | 521/149 |
| 4,908,392 | 3/1990 | Kusano et al. | 521/149 |

*Primary Examiner*—Morton Foelak
*Attorney, Agent, or Firm*—Connolly and Hutz

[57] ABSTRACT

The present invention relates to hydrophilic, swellable polymers which consists of radicals of the general formula I

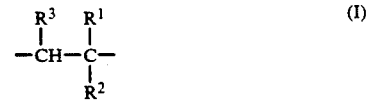

wherein $R^1$ to $R^3$ are defined as stated in the description, and of radicals of a crosslinking agent which have originated from monomers having at least two olefinically unsaturated double bonds, and which are characterized in that they are in the form of a highly porous, foam-like polyhedral structure, their preparation and their use as absorption agents for water and aqueous solutions.

6 Claims, No Drawings

HYDROPHILIC, SWELLABLE POLYMERS

The present invention relates to hydrophilic, swellable polymers, their preparation and their use.

Swellable polymers which absorb aqueous solutions are used for the production of tampons, nappies, sanitary towels and other hygiene articles and as water retention agents in horticultural farms.

Known absorption resins of this type include crosslinked carboxymethylcellulose, partly crosslinked polyalkylene oxide, hydrolysis products of starch-acrylonitrile graft copolymers and partly crosslinked polyacrylic acid salts.

All of these known polymers exhibit disadvantages, especially in the absorption of aqueous electrolyte solution as well as blood and urine.

According to the current prior art, the gel stabilities of the swollen polymer particles which are achieved at a high absorption capacity are too low. Tacky masses form, which impair the absorbency of the products produced with these substances.

It is known that the gel stability and the rate of liquid uptake can be increased by increasing the crosslinking density, but at the same time this reduces the absorption capacity. This procedure is undesirable inasmuch as the absorption capacity is the most important property of the polymer.

The object of the present invention is to provide polymers which absorb aqueous solutions which have a high rate of absorption and at the same time do not form tacky hydrogel particles of high gel stability in the swollen state.

This object is achieved, surprisingly, by hydrophilic, swellable polymers which consist, in random distribution, to the extent of 98 to 100% by weight of radicals of the general formula

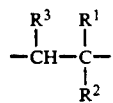
(I)

wherein $R^1$ denotes hydrogen, methyl or ethyl, $R^2$ denotes carboxyl, sulphonyl or phosphonyl, which can optionally be esterified by alkanol having 1 to 4 carbon atoms; phenyl; sulphonylphenyl; pyrrolidonyl; pyridyl; imidazolyl; a group of the formula

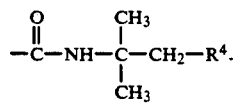

wherein $R^4$ represents the sulphonyl or the phosphonyl group; cyano; chlorine; the —$CONH_2$ group; ($C_1$–$C_4$)-alkanoyloxy; or a group of the formula

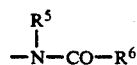

wherein $R^5$ and $R^6$ independently of one another denote hydrogen, methyl or ethyl or optionally also together represent trimethylene; and $R^3$ denotes hydrogen, methyl, ethyl or carboxyl, it also being possible for acid groups to be present in salt form, and to the extent of 0–2% by weight of radicals of a crosslinking agent which have originated from monomers having at least two olefinically unsaturated double bonds, and are characterized in that they are in the form of a highly porous, foam-like polyhedral structure.

The highly porous, foam-like polyhedral structure preferably has an average pore diameter of 0.8 to 1.2 mm.

The preferred density of the polymers according to the invention is between 0.01 and 0.05 g/cm³.

Preferred polymers according to the invention consist to the extent of 98.5 to 99.7% by weight of radicals of the general formula I and to the extent of 0.3 to 1.5% by weight of crosslinking structures.

In the polymers according to the invention, the radicals of the general formula I can all have exactly the same structure, but they can also differ from one another in respect of the radicals $R^1$, $R^2$ and $R^3$. In the latter case, radicals of the general formula I which differ in respect of the meanings of $R^1$, $R^2$ and $R^3$ can alternate in a random manner, but it is also possible for larger polymer sections in which $R^1$, $R^2$ and $R^3$ each have only one meaning to follow one another.

In the radicals of the general formula I, $R^1$ preferably denotes hydrogen or methyl. $R^2$ preferably represents carboxyl, sulphonyl or phosphonyl, carboxyl being particularly preferred. $R^3$ preferably denotes hydrogen.

In the radicals of the general formula I, all or some of the acid groups can be in salt form.

The alkali metal, alkaline earth metal, ammonium and amine salts are preferred. The sodium and ammonium salts are particularly preferred.

The crosslinking structures mentioned can be derived from all suitable monomers having at least two olefinically unsaturated double bonds.

Suitable monomers are, for example, compounds which contain at least two alkenyl groups, for example vinyl or allyl, or at least two alkenoyl groups, for example acrylate or methacrylate.

The crosslinking structures are preferably derived from monomers which contain 2, 3 or 4 ethylenically unsaturated double bonds.

The crosslinking structures are particularly preferably derived from methyl-bisacrylamide or N,N'-dihydroxyethylene-bisacrylamide. The crosslinking structures can furthermore also be derived from cationic monomers, such as, for example, diallyl-dimethylammonium chloride.

The polymers according to the invention can be prepared by polymerization of 98 to 100% by weight, preferably 98.5 to 99.7% by weight, of a compound of the general formula Ia

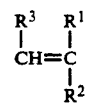
(Ia)

wherein $R^1$, $R^2$ and $R^3$ are as defined above, or a salt thereof, with 0 to 2% by weight, preferably 0.3 to 1.5% by weight, of a monomer having at least two olefinically unsaturated double bonds, characterized in that an aqueous matrix containing a surfactant and the monomers and stabilized by a liquid hydrocarbon phase is employed as the polymerization medium.

The polymerization medium preferably consists of 50 to 99.5% by weight of hydrocarbon, 0.2 to 20% by weight of monomer, 0.1 to 5% by weight of surfactant and 0.2 to 25% by weight of water.

The polymerization medium particularly preferably consists of 60 to 99% by weight of hydrocarbon, 0.4 to 16% by weight of monomer, 0.1 to 4% by weight of surfactant and 0.5 to 20% by weight of water.

The polymerization medium is preferably built up by foaming an aqueous solution containing surfactant and monomer, for which an inert gas, for example nitrogen, is preferably used, and then adding the liquid hydrocarbon.

During this operation, a quasi-foam structure is formed, the hydrocarbon phase occupying the position of the air in comparison with a conventional foam structure. Analogously to the air/water foam structure, here also the aqueous phase is the uninterrupted phase, that is to say continuous phase.

All the customary surfactants of anionic, cationic, and nonionic structure can be used as the surfactant. The surfactants of the following structures are preferred:

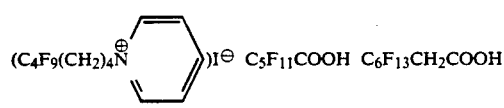

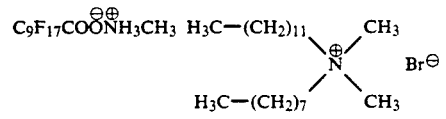

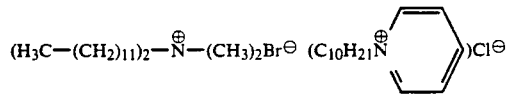

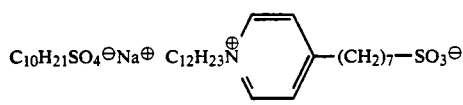

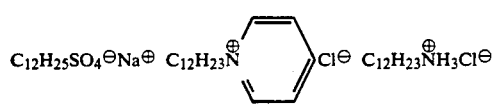

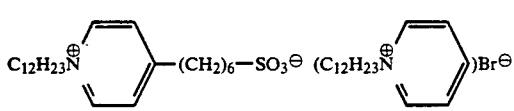

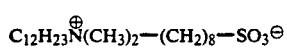

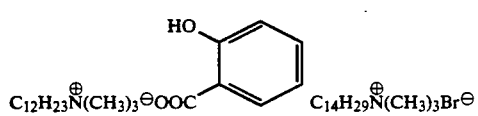

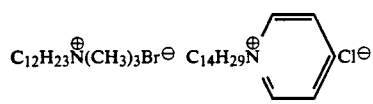

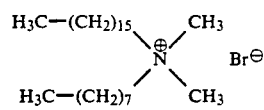

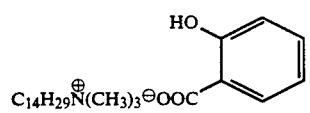

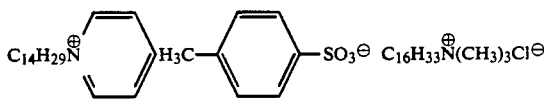

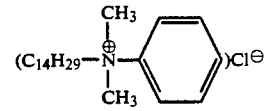

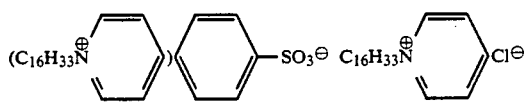

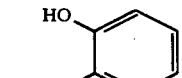

Sodium dodecylsulphate is an especially preferred surfactant.

Saturated and unsaturated aliphatics or aromatics can be used as the hydrocarbons. They can be employed by themselves or as mixtures with one another, in any desired mixing ratios.

Preferred hydrocarbons are n-pentane, n-hexane, n-heptene, n-octane, n-nonane, n-decane, n-dodecane, n-tetradecane, n-hexadecane, cyclohexane, cyclooctane, benzene, toluene, kerosine, petrol, lead-free petrol and diesel oil.

The monomers of the general formula Ia are preferably water-soluble, olefinically unsaturated compounds, acids, such as, for example, acrylic acid, methacrylic acid, vinylsulphonic acid, styrenesulphonic acid, maleic acid, fumaric acid, crotonic acid, 2-acrylamido-2-methyl-propanesulphonic acid, 2-acrylamido-2-methyl-propanephosphonic acid and vinylphosphonic acid and half-esters thereof, being particularly preferred. Suitable water-soluble monomers are, for example, also acrylamide, methacrylamide, vinylpyrrolidone, vinylpyridine, vinylimidazoline and N-vinylamides, such as, for example, N-vinyl-N-methyl-acetamide, N-vinyl-formamide and N-vinyl-acetamide.

Water-insoluble monomers can also be added as co-monomers within certain limits. Examples are the alkyl esters of acrylic and methacrylic acid, styrene, vinyl acetate, acrylonitrile and vinyl chloride.

Particularly stable polymers according to the invention are obtained if the monomer solution contains crosslinking agents, that is to say polyolefinically unsaturated compounds which effect three-dimensional crosslinking of the polymers. Examples of suitable monomers of this type are those having at least two alkenyl groups, such as vinyl or allyl, or at least two alkenoyl groups, such as acrylate or methacrylate. Particularly preferred crosslinking agents are methyl-bisacrylamide and N,N'-dihydroxyethylene-bisacrylamide.

The polymers according to the invention can be prepared in the process according to the invention by known polymerization reactions. Preferably, a polymerization of water-soluble monomers in aqueous solution is carried out. The polymerization, which proceeds relatively rapidly, is accelerated still further by the Norrish-Trommsdorff effect.

The polymerization reaction can be carried out in the temperature range between 0° C. and 130° C., preferably between 10° C. and 100° C., either under normal pressure or under increased pressure. As is customary, the polymerization can also be carried out in an inert gas atmosphere, preferably under nitrogen.

High-energy electromagnetic radiation or the customary chemical polymerization initiators can be used to initiate the polymerization reaction, for example organic peroxides, such as benzoyl peroxide, tert.-butyl hydroperoxide, methyl ethyl ketoneperoxide, cumene hydroperoxide, azo compounds, such as azo-di-isobutyro-nitrile, and inorganic peroxy compounds, such as $(NH_4)_2S_2O_8$ or $K_2S_2O_8$ or $H_2O_2$, if appropriate in combination with reducing agents, such as sodium bisulphite, and iron(II) sulphate or redox systems which contain as the reducing component an aliphatic and aromatic sulphinic acid, such as benzenesulphinic acid and toluenesulphinic acid or derivatives of these acids, such as, for example, Mannich adducts of sulphinic acid, aldehydes and amino compounds, such as are described in German Patent Specification 1,301,566. As a rule, 0.03 to 2 g of the polymerization initiator are employed per 100 g of total monomers.

After removal of the solvent, hydrocarbon and surfactant, the process according to the invention gives highly absorbent, porous polymer structures which are outstandingly suitable as absorption agents for water and aqueous solutions, so that they can advantageously be employed as water retention agents in horticultural farms, as filtration auxiliaries and in particular as absorbent components in hygiene articles, such as nappies, tampons and sanitary towels.

EXAMPLE 1

A solution of 2 g of acrylic acid, 2 g of sodium dodecylsulphate and 0.1 g of N,N'-(1,2-dihydroxyethylene)-bisacrylamide in 4.9 g of distilled water is prepared and initially introduced into the reaction vessel together with 40 g of heptane.

To remove the oxygen in the solution, nitrogen is passed through the system with the aid of a glass capillary over a period of five minutes. The vessel is now closed with a stopper and the mobile two-phase system is converted into a gelatinous state by shaking movements. The gel formation is complete when all the heptane has been incorporated into the gel phase. 0.018 g of potassium peroxodisulphate in 0.882 g of water, and 200 μl of 10% strength ascorbic acid solution are now added and shaken into the gel substance. A start to the polymerization is achieved within 60 minutes in this manner. The start of the polymerization is clearly recognizable from an increase in temperature of about 15° C. The reaction is complete about 10 to 15 minutes after the start of polymerization.

The polymer substance is now transferred to a dish and treated for about 8 hours with a solution of 1.4 g of $NaHCO_3$ in an amount of water which is just sufficient to cover the polymer completely. During this period, the size of the cells filled with hydrocarbon increases from about 20–40 μm in diameter to about 0.8 to 1.2 mm. Liquid nitrogen is now poured over the very soft and unstable product and the product is freeze-dried for 30 minutes in a microwave oven (alternatively, this can also be carried out in a freeze-dryer or rotary evaporator. Time required in this case about 8 hours).

The product formed is distinguished by a sponge-like structural pattern penetrated by an open, three-dimensional system of channels. The pore width is 0.8 to 1.2 mm. The density is in the range from 0.01 to 0.5 g/cm$^3$.

The following tabular Examples 2 to 36 are prepared analogously to Example 1. In the table, the quantity data denote per cent by weight, based on the total amount used in the reaction.

The following abbreviations are used:
AA: acrylic acid
AMP: 2-acrylamido-2-methyl-propanesulphonic acid
AAM: acrylamide
MA: methylacrylate
TAE: tetraallyloxyethane
DHEBA: N,N'-dihydroxyethylene-bisacrylamide
MBA: methyl-bisacrylamide
KPS: $K_2S_2O_8$
$H_2O_2$: hydrogen peroxide
APS: $(NH_4)_2S_2O_8$

TABLE

| Example | Monomer | Comonomer | Crosslinking Agent | Initiator | Hydrocarbon | Surfactant % by weight | Monomer % by weight | Comonomer % by weight | Crosslinking agent % by weight | Initiator % by weight | $H_2O$ % by weight | Hydrocarbon % by weight |
|---|---|---|---|---|---|---|---|---|---|---|---|---|
| 2 | AA | | TAE | KPS | pentane | 1.5 | 9 | | 0.45 | 0.09 | 18.96 | 70 |
| 3 | AA | | TAE | KPS | hexane | 1 | 6 | | 0.3 | 0.06 | 12.64 | 80 |
| 4 | AA | | TAE | KPS | heptane | 0.5 | 3 | | 0.15 | 0.03 | 6.05 | 90 |
| 5 | AA | | TAE | KPS | octane | 0.25 | 1.5 | | 0.075 | 0.015 | 3.16 | 95 |
| 6 | AA | | TAE | KPS | diesel oil | 0.1 | 0.6 | | 0.03 | 0.006 | 1.26 | 98 |
| 7 | AA | | DHEBA | APS | heptane | 1.5 | 6 | | 0.45 | 0.09 | 21.96 | 70 |
| 8 | AA | | DHEBA | APS | decane | 1 | 4 | | 0.3 | 0.06 | 14.64 | 80 |
| 9 | AA | | DHEBA | APS | pentane | 0.5 | 2 | | 0.15 | 0.03 | 7.05 | 90 |
| 10 | AA | | DHEBA | APS | hexane | 0.25 | 1 | | 0.075 | 0.015 | 3.66 | 95 |
| 11 | AA | | DHEBA | APS | nonane | 0.1 | 0.4 | | 0.03 | 0.006 | 1.464 | 98 |
| 12 | AAM | | DHEBA | KPS | pentane | 1.5 | 12 | | 0.45 | 0.09 | 15.96 | 70 |
| 13 | AAM | | DHEBA | KPS | hexane | 1 | 8 | | 0.3 | 0.06 | 10.64 | 80 |
| 14 | AAM | | DHEBA | KPS | heptane | 0.5 | 4 | | 0.15 | 0.03 | 5.05 | 90 |
| 15 | AAM | | DHEBA | KPS | dodecane | 0.25 | 2 | | 0.075 | 0.015 | 2.66 | 95 |
| 16 | AAM | | DHEBA | KPS | octane | 0.1 | 0.8 | | 0.03 | 0.006 | 1.064 | 98 |
| 17 | AMP | | MBA | KPS | pentane | 6 | 9 | | 0.3 | 0.06 | 14.64 | 70 |
| 18 | AMP | | MBA | KPS | hexane | 4 | 6 | | 0.2 | 0.04 | 9.76 | 80 |
| 19 | AMP | | MBA | KPS | heptane | 2 | 3 | | 0.1 | 0.02 | 4.88 | 90 |
| 20 | AMP | | MBA | KPS | decane | 1 | 1.5 | | 0.05 | 0.01 | 2.44 | 95 |

TABLE-continued

| Example | Monomer | Comonomer | Crosslinking Agent | Initiator | Hydrocarbon | Surfactant % by weight | Monomer % by weight | Comonomer % by weight | Crosslinking agent % by weight | Initiator % by weight | H₂O % by weight | Hydrocarbon % by weight |
|---|---|---|---|---|---|---|---|---|---|---|---|---|
| 21 | AMP | | MBA | KPS | diesel oil | 0.4 | 0.6 | | 0.02 | 0.004 | 0.976 | 98 |
| 22 | AA | MA | DHEBA | KPS | pentane | 6 | 3 | 3 | 0.3 | 0.06 | 17.64 | 70 |
| 23 | AA | MA | DHEBA | KPS | hexane | 4 | 1 | 3 | 0.2 | 0.04 | 11.76 | 80 |
| 24 | AA | MA | DHEBA | KPS | heptane | 2 | 1.5 | 0.5 | 0.1 | 0.02 | 5.88 | 90 |
| 25 | AA | MA | DHEBA | KPS | octane | 1 | 0.5 | 0.5 | 0.05 | 0.01 | 2.94 | 95 |
| 26 | AA | MA | DHEBA | KPS | nonane | 0.4 | 0.1 | 0.3 | 0.02 | 0.004 | 1.176 | 98 |
| 27 | AAM | | TAE | H₂O₂ | pentane | 6 | 6 | | 0.3 | 0.06 | 17.64 | 70 |
| 28 | AAM | | TAE | H₂O₂ | hexane | 4 | 4 | | 0.2 | 0.04 | 11.76 | 80 |
| 29 | AAM | | TAE | H₂O₂ | heptane | 2 | 2 | | 0.1 | 0.02 | 5.88 | 90 |
| 30 | AAM | | TAE | H₂O₂ | octane | 1 | 1 | | 0.05 | 0.01 | 2.94 | 95 |
| 31 | AAM | | TAE | H₂O₂ | nonane | 0.4 | 0.4 | | 0.02 | 0.004 | 1.176 | 98 |
| 32 | AA | | DHEBA | APS | decane | 6 | 12 | | 0.3 | 0.6 | 11.64 | 70 |
| 33 | AA | | DHEBA | APS | cyclohexane | 4 | 8 | | 0.2 | 0.04 | 7.76 | 80 |
| 34 | AA | | DHEBA | APS | benzene | 2 | 4 | | 0.1 | 0.02 | 3.88 | 90 |
| 35 | AA | | DHEBA | APS | toluene | 1 | 2 | | 0.05 | 0.01 | 1.94 | 95 |
| 36 | AA | | DHEBA | APS | diesel oil | 0.4 | 0.8 | | 0.02 | 0.004 | 0.776 | 98 |

What is claimed is:

1. Hydrophilic, swellable polymer which consists in random distribution, to the extent of 98 to 100% by weight of radicals of the general formula I

wherein $R^1$ denotes hydrogen, methyl or ethyl, $R^2$ denotes carboxyl, or carboxyl which is esterified by alkanol having 1 to 4 carbon atoms; and $R^3$ denotes hydrogen, methyl, ethyl or carboxyl, it also being possible for acid groups to be present in salt form, and to the extent of 0–2% by weight of radicals of a crosslinking agent which having originated from monomers having at lest two olefinically unsaturated double bonds, characterized in that it is in the form of a highly porous, foam-like polyhedral structure.

2. Polymer according to claim 1, characterized in that the polyhedral structure has an average pore diameter of 0.8 to 1.2 mm.

3. Polymer according to claim 1, characterized in that it consists to the extent of 98.5 to 99.7% by weight of radicals of the general formula I and to the extent of 0.3 to 1.5% by weight of crosslinking structures 4. Polymer according to claim 1, characterized in that in the general formula I, $R^1$ denotes hydrogen or methyl, $R^2$ denotes carboxyl, and $R^3$ denotes hydrogen.

5. Polymer according to claim 1, characterized in that the radicals of a crosslinking agent are derived from methyl-bisacrylamide or N,N'-dihydroxyethylene-bisacrylamide.

6. Polymer according to claim 1, wehrein the density of the polymer is between 0.01 and 0.05 g/cm³.

* * * * *